(12) United States Patent
Roberts et al.

(10) Patent No.: US 6,986,897 B1
(45) Date of Patent: Jan. 17, 2006

(54) ALCOHOL-FREE ANTI-BACTERIAL WIPES

(75) Inventors: Joseph T. Roberts, Edison, NJ (US); Carol A. Duden-Antenna, Lambertville, NJ (US); Shaw Kong Chang, Belle Mead, NJ (US); Walter J. Hines, Neshanic Station, NJ (US); Joseph Librizzi, Neshanic, NJ (US)

(73) Assignee: Johnson & Johnson Consumer Companies, Inc., Skillman, NJ (US)

(*) Notice: Subject to any disclaimer, the term of this patent is extended or adjusted under 35 U.S.C. 154(b) by 329 days.

(21) Appl. No.: 09/632,992

(22) Filed: Aug. 4, 2000

Related U.S. Application Data

(63) Continuation-in-part of application No. 09/411,552, filed on Oct. 4, 1999, now abandoned.

(51) Int. Cl.
*A61K 7/075* (2006.01)
*A61K 9/00* (2006.01)
*A01N 25/34* (2006.01)

(52) U.S. Cl. .................. 424/402; 424/400; 424/401; 424/404; 424/70.21; 510/130

(58) Field of Classification Search .............. 424/402, 424/404, 443; 514/772, 772.1, 772.4, 772.6
See application file for complete search history.

(56) References Cited

U.S. PATENT DOCUMENTS

| | | |
|---|---|---|
| 3,624,224 A | 11/1971 | Wei et al. |
| 4,326,977 A | 4/1982 | Schmolka |
| 4,551,377 A | 11/1985 | Elves et al. |
| 4,588,457 A | 5/1986 | Crenshaw et al. |
| 4,725,489 A | 2/1988 | Jones et al. |
| 4,740,398 A | 4/1988 | Bouchette |
| 4,753,844 A | 6/1988 | Jones et al. |
| 4,817,790 A | 4/1989 | Porat et al. |
| 4,904,524 A | 2/1990 | Yoh |
| 4,990,334 A | 2/1991 | Longino et al. |
| 4,998,984 A | 3/1991 | McClendon |
| 5,049,440 A | 9/1991 | Bornhoeft, III et al. |
| 5,292,581 A | 3/1994 | Viazmensky et al. |
| 5,366,732 A * | 11/1994 | Zighelboim ............. 424/411 |
| 5,558,873 A | 9/1996 | Funk et al. |
| 5,576,006 A | 11/1996 | Smith |
| 5,620,694 A | 4/1997 | Girardot |
| 5,661,170 A | 8/1997 | Chodosh |
| 5,662,991 A | 9/1997 | Smolik et al. |
| 5,702,992 A | 12/1997 | Martin et al. |
| 5,707,736 A | 1/1998 | Levy et al. |
| 5,744,149 A | 4/1998 | Girardot |
| 5,753,246 A | 5/1998 | Peters |
| 5,858,936 A | 1/1999 | Tamura et al. |
| 6,114,298 A * | 9/2000 | Petri et al. ............. 510/372 |
| 6,149,926 A * | 11/2000 | Venkitaraman et al. ..... 424/402 |
| 6,153,208 A * | 11/2000 | McAtee et al. ........... 424/402 |

FOREIGN PATENT DOCUMENTS

| | | |
|---|---|---|
| CA | 1186499 | 5/1985 |
| CA | 1252604 | 4/1989 |
| CA | 1265740 | 2/1990 |
| CA | 1274771 | 10/1990 |
| CA | 1308241 | 10/1992 |
| CA | 1325560 | 12/1993 |
| CA | 1834320 | 2/1995 |
| CA | 2135871 A1 | 5/1995 |
| CA | 2177038 | 6/1995 |
| CA | 2204621 | 5/1996 |
| CA | 2164528 | 6/1996 |
| CA | 2212685 | 8/1996 |
| CA | 2214507 | 10/1996 |
| CA | 2218703 | 10/1996 |
| CA | 2225147 | 1/1997 |
| CA | 2225161 | 1/1997 |
| CA | 2229452 | 2/1997 |
| CA | 2234205 | 5/1997 |
| CA | 2252892 | 11/1997 |
| CA | 2253357 | 11/1997 |
| CA | 2273816 | 11/1997 |
| CA | 2269296 | 5/1998 |
| CA | 2269477 | 5/1998 |
| CA | 2269505 | 5/1998 |
| CA | 2269601 | 5/1998 |
| CA | 2269602 | 5/1998 |
| CA | 2269604 | 5/1998 |
| CA | 2233371 | 10/1998 |
| CA | 2233548 | 10/1998 |
| CA | 2235846 | 10/1998 |
| CA | 2245628 | 2/1999 |
| CA | 2256659 | 6/1999 |

OTHER PUBLICATIONS

Label: Johnson's Antibacterial Towelettes, announced to trade: Oct. 1999.
Technical Data F-4575, The Steams Technical Textiles Company, Oct. 13, 1993.
21 CFR Parts 333 & 369, vol. 59, No. 116, (Jun. 17, 1994) (Tentative Final Monograph for Health Care Antiseptic Drug Products, Proposed Rule) as cited in 59 FR 31402.

* cited by examiner

*Primary Examiner*—Thurman K. Page
*Assistant Examiner*—Sharon Howard

(57) ABSTRACT

An alcohol-free antibacterial wipe comprising a flexible fabric coated with a polymeric latex binder, and an aqueous antibacterial solution wherein the aqueous antibacterial solution is comprised of an effective amount of a cationic antibacterial agent and sufficient amount of a surfactant.

8 Claims, No Drawings

ALCOHOL-FREE ANTI-BACTERIAL WIPES

CROSS-REFERENCE TO RELATED APPLICATION

This application is a continuation-in-part application of U.S. application Ser. No. 09/411,552 filed on 4 Oct. 1999 (now abandoned), which is incorporated herein by reference in its entirety.

FIELD OF THE INVENTION

This invention relates to an alcohol-free anti-bacterial wipe that comprises a cationic antimicrobial agent as its primary active antibacterial agent at a concentration preferably within OTC monograph levels, while maintaining consumer acceptable aesthetics.

BACKGROUND OF THE INVENTION

There are a number of antibacterial wipes on the market and most of them contain high levels of alcohol. Typically, the alcohol acts in two ways, first as an antimicrobial agent, either solely or in combination with other antimicrobial agents, and second as an agent to improve drying time after wiping. However, the use of alcohol has some drawbacks. Particularly, alcohol dries the skin by removing essential oils and alcohol can be lethal if ingested by infants and small children.

To eliminate problems with alcohol, several non-alcohol containing antibacterial wipes have been developed. However, there are many properties of these wipes upon which could be improved.

For example, one potential drawback of alcohol-free wipes is the loss of perceived wet feel of the wipe. Since alcohol reduces surface tension, wipes that contain alcohol will wet the surface of the skin well, thus, giving the user a good perception of wetness. This feeling of wetness has been identified by consumers as a desirable characteristic for wipes. In order to compensate for the lack of alcohol, alcohol-free wipes must contain some level of surfactant that lowers the surface tension of the aqueous solution, and thereby, improving the wetting of the skin. Although surfactants are effective at lowering surface tension, their use for this purpose has several potential drawbacks that can affect consumer perception. Examples of some of these problems are excessive foaming while wiping and a "tacky" after feel. Thus, the importance of selecting an appropriate surfactant for this use is paramount.

In addition, the choice of antimicrobial agent in an alcohol-free wipe is limited to agents which are soluble in water and are safe and effective. Particularly, when wipes are used on children, the choice of anitmicrobial agent must be one which is proven safe and effective for subjects of all ages. There are certain antimicrobial agents which can be used safely in wipe products, such as benzalkonium chloride. However, due to the nature of the wipe fabric, it is often difficult to maintain the concentration of said antimicrobial agents in a wipe at the levels published in the appropriate OTC monograph levels for an antiseptic product. See 21 CFR Parts 333 and 369; Vol. 59, No. 116, Jun. 17, 1994; "Tentative Final Monograph for Health-Care Antiseptic Drug Products; Proposed Rule". The OTC monograph sets levels of 0.10% to 0.13%, (±10%) for benzalkonium chloride in an antiseptic product.

In addition to the aforementioned issues, currently marketed alcohol-free wipes are forced to use fabrics that contain high loads of binder, e.g. about 50% to about 70% binder with respect to the overall wipe weight. The binder is present to reduce adsorption of the antimicrobial agent to the fabric. Disadvantageously, fabrics possessing large quantities of binders tend to be rather stiff or "boardy", and hence, are not preferred by consumers.

Accordingly, it would be highly desirable to develop an alcohol-free antibacterial wipe which meets the consumer's needs for a wipe that is flexible and has a wet feel. Particularly, it is desirable to produce an alcohol-free wipe that uses a safe and effective antimicrobial agent in a manner which preferably meets the proposed OTC monograph levels of an antimicrobial agent. The unmet need for an alcohol-free antibacterial wipe which is safe and effective for infants, children, and adults while maintaining good consumer aesthetics, is the subject of this invention.

SUMMARY OF THE INVENTION

This invention relates to an alcohol-free antibacterial wipe comprising a flexible fabric containing a latex binder, and an aqueous antibacterial solution wherein the aqueous antibacterial solution comprises an effective amount of a cationic antibacterial agent and a sufficient amount of a surfactant and the binder is present in at least about 90% of the substrate thickness.

Further, the invention relates to a method of preparing an alcohol-free antibacterial wipe which comprises
  (i) preparing a solution of a cationic antibacterial agent, a surfactant, and water; and
  (ii) combining said solution with a flexible fabric that is coated with a latex binder, wherein the binder is present in at least about 90% of the substrate thickness.

DETAILED DESCRIPTION OF THE INVENTION

This invention relates to an alcohol-free antibacterial wipe comprising a flexible fabric coated with a latex binder and an aqueous antibacterial solution where said aqueous antibacterial solution comprises an effective amount of a cationic antibacterial agent and a sufficient amount of a surfactant.

As used herein, the term "flexible fabric" refers to a fabric that does not possess a boardy feel to consumers. Flexible fabrics suitable for use in this invention include the non-woven fabrics such as those which contain about 10% to about 100% rayon. In addition, these flexible fabrics may be hydroentangled or air-laided and coated with a binder or extruded and held together with a binder. These flexible fabrics typically have a basis weight of 90 gsm (gram/square meter) to 10 gsm. The preferred flexible fabrics of the invention are about 20% to about 100% rayon. Fabrics which are extruded and held together with a polymer latex binder are particularly preferred. The preferred basis weight for these flexible fabrics is from about 25 gsm to about 40 gsm. The particularly preferred basis weight is about 30 gsm to about 38 gms. The preferred flexible fabric of the invention is extruded 100% rayon which is held together with a polymer latex binder and has a basis weight of about 30 gms to about 38 gms. A commercial example of a desirable fabric is Stearns F-4575 available from Steams, Inc. This fabric is coated with a polymer latex binder, E32 Special Latex Binder.

Suitable latex binders for the fabrics include those polymerized from at least one acrylic monomer, and in particular include those binders comprised of, based upon the total weight of binder, a mixture of from about 70% to about 90% of a first self-crosslinking acrylic emulsion polymer, and preferably such a polymer having a Tg of from about 0° C. to about 10° C. and more preferably about 5° C., and from about 10% to about 30% of a second acrylic emulsion polymer, and preferably such a polymer having a Tg of from about 20° C. to about 40° C., and more preferably about 34° C. In one embodiment, the first self-crosslinking acrylic emulsion polymer is non-ionic, and the second acrylic emulsion polymer is anionic. A preferable latex binder is the "E32 Special Latex Binder," which is comprised of a mixture of about 80% by weight of a self-crosslinking acrylic emulsion polymer latex binder available from the Rohm and Haas Company under the tradename, "RHOPLEX® E32 NP" and about 20% by weight of an acrylic emulsion polymer latex binder available from the Rohm and Haas Company under the tradename, "RHOPLEX® TR407."

The flexible fabric substrates of the present invention typically contain, based upon the total weight of the substrate, from about 25 percent to less than about 40 percent, e.g. from about 25 percent to about 35 percent, of suitable binder.

The phrase "cationic antibacterial agent" refers to quaternary ammonium compounds. Examples of such compounds include but are not limited to benzalkonium chloride, benzethonium chloride, cetylpyridinium chloride and the like, and mixtures thereof. The preferred cationic antibacterial agent is benzalkonium chloride.

"Effective amount," refers to the concentration of cationic antibacterial agent which is present in the aqueous antibacterial solution once said flexible fabric has been combined with said aqueous antibacterial solution. Typically, said cationic antibacterial which are present in the aqueous antibacterial solution at a concentration (weight/weight) of from about 0.05% to about 0.5%, preferably from about 0.15% to about 0.30%, and more preferably from about 0.09% to about 0.15%. The preferred cationic antibacterial agent is benzalkonium chloride and this agent at a concentration of about 0.09% to about 0.15%.

The "surfactants" which are used in this invention are nonionic surfactants, amphoteric surfactants, or mixtures thereof. Examples of amphoteric surfactants include but are not limited to alkylimino-diprorionates, alkylamphoglycinates (mono or di), alkylamphoproprionates (mono or di) alkylamphoacetates (mono or di), N-alkyl β-aminoproprionic acids, alkylpolyamino carboxylates and phosphorylated imidazolines. The preferred amphoteric surfactants are disodium lauroamphodiacetate, sodium lauroampho PG-acetate, sodium cocoamphoacetate, and disodium cocamphodipropionate. The particularly preferred amphoteric surfactants are disodium lauroamphodiacetate. One commercial supplier of this material is Mona Industries under the tradename Monateric 949-J. The nonionic surfactants include the fatty alcohol acid or amide ethoxylates, monoglyceride ethoxylates, sorbitan ester ethoxylates, and alkyl polyglycosides. The preferred non-ionic surfactants are PEG-6 caprylic/capric glycerides (available from Croda, Inc., Parsippany, N.J.), polysorbate 20, and PEG-80 sorbitan laurate (available form Uniqema, Wilmington Del.). The overall particularly preferred surfactant of the invention is disodium lauroamphodiacetate.

As used herein the phrase "sufficient amount" refers to the amount of surfactant that is necessary to produce a wet feel to the consumer without tackiness. Typically most commercially available surfactants contain an active percentage of the surfactant along with some other components. For purposes of this invention, the term sufficient amount" refers to the percentage by weight of active amount of the surfactant to the weight of the aqueous composition. When using an amphoteric surfactant, the sufficient amount is typically, based upon the total weight of the solution, from about 0.01% to about 10%, preferably from about 0.05% to 5%, and more preferably, from about 0.10% to about 0.5%. When using a nonionic surfactant, the sufficient amount is typically, from about 0.02% to about 15%, preferably, from about 0.10% to about 10%, and more preferably from about 0.25% to about 2%.

Further, the invention relates to a method of preparing an alcohol-free antibacterial wipe which comprises
(i) preparing a solution of an cationic antibacterial agent, a surfactant, and water; and
(ii) combining said solution with a flexible fabric containing a binder such that the binder is present in at least about 90% of the substrate thickness.

The terms "cationic antibacterial agent," "surfactants," and "flexible fabric," have their aforementioned meanings and preferred definitions. Typically the percentage by weight of the cationic antibacterial agent with respect to the weight of said solution is about 0.1% to about 0.5%, more preferably about 0.15% to about 0.3%, more preferably about 0.20% to about 0.23%. Typically the percentage by weight of the surfactant with respect to the weight of said solution is about 0.1% to about 10%, more preferably about 0.5% to about 5%, more preferably about 0.10% to about 1.0%. Typically the percentage by weight of the water with respect to the weight of said solution is about 85% to about 99.5%, more preferably about 90% to about 99%, more preferably about 95% to about 99%.

For example the antibacterial wipes of the invention may be prepared by feeding a flexible fabric into a folding machine. The machine fan folds said flexible fabric into four panels, cutting to a length of six inches and then folding said flexible fabric into thirds. Said flexible fabric comprises 75% pulp, 20% rayon, and 5% polyester/polyethylene where said flexible fabric substrate has a basis weight of 55 gsm and is coated with a latex binder such that the binder is present in at least about 90% and preferably about 100% of the substrate thickness. The appropriately sized flexible fabric is inserted into packet and sealed on three sides, about 4.09 mL of the aqueous antibacterial solution is added to the packet via a piston pump. The fourth side of the packet is sealed on the fourth side and then dispensed from the machine.

The antibacterial solution may also be applied to the fabric substrate via any other means known in the art such as via spray coating.

In one embodiment, the binder is first applied to the substrate in a manner such that it penetrates greater than about 90% and preferably about 100% of the substrate thickness, i.e., not only the front and back substrate surfaces are preferably coated with binder but also the binder is absorbed into the substrate material itself. Then, the antibacterial solution is applied to the coated substrate.

In a preferred embodiment, the binder is similarly applied such that it coats the entire front and back surfaces of the substrate and is absorbed into the entire substrate material itself prior to the application of antibacterial solution thereto.

We have unexpectedly found that the stability of the antibacterial solution applied to the wipe product of the present invention is greatly improved when the binder penetrates greater than about 90% and preferably about 100% of the substrate thickness.

The wipes of the present invention may either be single ply or multiply, e.g. two ply substrates laminated to each other via means well known in the art. When removed from its container, the wipes of the present invention are not only sufficiently wet, and thus do not require further wetting in order to activate the antibacterial agent contained therein, but also possess a soft feel to the touch.

In order to illustrate the invention the following examples are included. These examples do not limit the invention. They are meant only to suggest a method of practicing the invention. Those knowledgeable in the preparation of wipe products as well as other specialties may find other methods of practicing the invention. However, those methods are deemed to be within the scope of this invention.

EXAMPLES

Example 1

Preparation of Aqueous Antibacterial Solution A

The ingredients listed in Table A were mixed as follows.

Step 1: Component amounts in this procedure are given in terms of parts by weight to prepare 100 parts of the aqueous antibacterial solution A. 98.8 parts of water are added to the main mix vessel.

Step 2: 0.44 Parts of benzalkonium chloride solution (50%) is weighed in a separate container and then added to the main mixing vessel under agitation and mix well for 10 minutes or until uniform.

Step 3: In a separate container, weigh 0.50 parts of disodium lauroamphodiacetate. In the same container, add 0.06 parts of fragrance. Agitiate the disodium lauroamphodiacetate and fragrance mixture until homogenous.

Step 4: Under continuous agitation, add the fragrance and disodium lauroamphodiacetate premix to the main mix vessel and mix well for 10 minutes or until uniform.

Step 5: 0.20 Parts of disodium EDTA is weighed in a separate container and then added to the main mixing vessel under agitation and mix well for 20 minutes or until uniform.

Step 6: If necessary, adjust Ph to 6.0 with 10% citric acid solution.

TABLE A

| INCI Name | % Active | % (wt/wt) | % Active (wt/wt) |
|---|---|---|---|
| Disodium Lauroamphodiacetate | 30 | 0.5000 | 0.1500 |
| Benzalkonium Chloride Solution | 50 | 0.4400 | 0.2200 |
| Disodium EDTA | 30 | 0.2000 | 0.0600 |
| Fragrance | 100 | 0.0600 | 0.0600 |
| Water | 0 | 98.800 | 0.0000 |

Example 2

Method of Determining Benzalkonium Chloride Concentration

The following discussion describes the Benzalkonium Chloride Test Procedure in the expressed solution of this antibacterial wipe. Five wipes are placed into a 30 ml disposable syringe with plunger removed. The plunger is then inserted and pressed to express the liquid from the wipes into a disposable centrifuge tube, pressing hard to collect as much expressed solution as possible. A representative aliquot of the expressed solution is then transferred into an HPLC vial. The concentration of benzalkonium chloride in the expressed solution is determined by the Reverse Phase HPLC (High Performance Liquid Chromatography). The C12, C14 and C16 homologs of benzalkonium chloride are separated from each other and from other components in the expressed solution on a Supelco 25 cm×4.6 mm, 5 microns Supelcosil LC-CN column and detected by and a Ultraviolet detector at 260 nm. The quantitation is performed by the method of external standardization compared to a benzalkonium standard solution of approximately at 1.3 to 1.4 mg/ml concentrations. The mobil phase is prepared by adding 650 ml acetonitrile to 350 ml pH 5.0 0.1 M Ammonium Acetate Buffer and 1 ml of triethylamine. The injection volume is 25 microliters, flow rate is 1.7 ml/min and the column temperature is 40 C.

Example 3

Fabric Selection

Aqueous antibacterial solutions containing a variety of different benzalkonium chloride ("BZK") concentrations were prepared following the general procedure of Example 1. Solution was applied to the fabrics in a quantity equivalent to 350% of the fabric weight as determined by the area and basis weight of the fabric as shown in Table B. The generic term for each fabric is listed with the tradename for each fabric. Each sample was tested when prepared to determine the percentage of benzalkonium chloride ("BZK") present in the prepared product by the procedure of Example 2 (initial). Subsequently, all samples were stored at 40° C. and were tested over a 13 week period at days 1 through 14 and weeks 3, 4, 8, and 13. The tests were discontinued if the BZK level in the expressed solution was above 0.15% or below 0.09% at any point after seven days from manufacture was above 0.15%. The goal is to prepare a wipe which maintains a BZK level which meets the standard of the OTC monograph, between 0.10% to 0.13%±10% over 13 weeks.

TABLE B

| Fabric Composition | Tradename | BZK | Stability Results |
|---|---|---|---|
| Hydroentangled 75% pulp 20% rayon 5% polyester/polyethylene basis wt 55 gsm no binder | Dexter Hydraspun 10180 | 0.44% | Initial - 0.27% 3 w@40° C. - 0.108% this experiment was terminated at 3 weeks due to the rapid degradation of BZK |
| Hydroentangled 65% pulp 30% rayon 5% polyester/polyethylene basis wt 60 gsm no binder | Dexter Hydraspun 10234 | 0.44% | Initial - 0.12% 3 w@40° C. - 0.068% |
| Hydroentangled 55% pulp 40% rayon 5% polyester/polyethylene basis wt 58 gsm with latex binder | Dexter Hydraspun 10444 | 0.44% | Initial - 0.25% 8 days@40° C. - 0.118% this experiment was terminated at 8 days due to the rapid degradation of BZK |
| Hydroentangled 65% rayon, 35% polyester basis wt 55 gsm no binder | Dupont Sontara 8462 | 0.44% | Initial - 0.39% 7 days@40° C. - 0.167% |
| Spunlace 100% rayon basis wt 38 gsm with E358 latex binder | Stearns F-4657 | 0.20% | Initial - 0.185% 7 days@40° C. - 0.07% |
| 100% rayon, basis wt 38 gsm with E 32 Special latex binder penetrating through about >90% of the substrate thickness | Stearns F-4575 | 0.27% | Initial - 0.102% 13 w@40° C. - 0.141% |

Example 4

Test to Determine the Appropriate Initial Benzalkonium Chloride Level

The results of Example 3 indicated that the 100% rayon fabric with a basis weight of 38 gms and a special latex binder was the appropriate fabric. The procedures of examples 1, 2, and 3 were repeated on this fabric using different concentrations of BZK in the aqueous antibacterial solution. The fabric and the initial BZK levels are listed in columns 1 and 2 of Table C, respectively. Column 3 lists the initial BZK levels as well as the levels at a particular time period.

TABLE C

| Fabric | BZK Level | Stability Results |
|---|---|---|
| 100% rayon Stearns F-4575 Basis wt 38 gsm With E 32 Special latex binder penetrating through about >90% of the substrate thickness | 0.27% | Initial - 0.179% 13 w@40° C. - 0.148% |
| 100% rayon Stearns F-4575 Basis wt 38 gsm With E 32 Special latex binder penetrating through about >90% of the substrate thickness a | 0.28% | Initial - 0.183% 13 w@40° C. - 0.167% |
| 100% rayon Stearns F-4575 Basis wt 38 gsm With E 32 Special latex binder | 0.33% | Initial - 0.203% 8 w@40° C. - 0.199% |
| 100% rayon Stearns F-4575 Basis wt 38 gsm With E 32 Special latex binder | 0.28% | Initial - 0.153% 8 w@40° C. - 0.172 |
| 100% rayon Stearns F-4575 Basis wt 38 gsm With E 32 Special latex binder | 0.25% | Initial - 0.125% 8 w@40° C. - 0.141% |
| 100% rayon Stearns F-4575 Basis wt 38 gsm With E 32 Special latex binder | 0.23% | Initial - 0.102% 4 w@40° C. - 0.141 |
| 100% rayon Stearns F-4575 Basis wt 38 gsm With E 32 Special latex binder | 0.23% | Initial - 0.11% 4 w@40° C. - 0.142% |

Example 5

Surfactant Selection

A number of surfactants were tested to determine whether they were suitable for use with alcohol-free antibacterial wipes. The fabric which was used for all examples was the 100% rayon fabric with a basis weight of 38 gsm and a polymer latex binder. All products were prepared using an aqueous solution with 0.21% benzalkonium chloride. Each final product was evaluated by ten (10) consumers to determine whether the wetness and the general consistency of the wipes was acceptable. The results of the testing along with the surfactant tested (tradenames are in parenthesis) are listed in Table D.

TABLE D

| Formula | Surfactant | Consumer Evaluation |
|---|---|---|
| 8726-092 | 0.50% PEG-6 Caprylic/Capric Glycrides (Glycerox 767) | Unacceptable - tacky afterfeel |

TABLE D-continued

| Formula | Surfactant | Consumer Evaluation |
|---|---|---|
| 8726-101 | 0.30% PEG-6 Caprylic/Capric Glycrides (Glycerox 767) | Unacceptable - tacky afterfeel |
| 8726-102 | 0.15% PEG-6 Caprylic/Capric Glycrides (Glycerox 767) | Unacceptable - tacky afterfeel |
| 8726-112 | 0.50% Disodium Lauroamphodiacetate (Monateric 949J) | Acceptable - superior afterfeel, low foam |
| 8726-114 | 0.10% Cocamidopropylamine Oxide (Ammonyx CDO) | Unacceptable - too much foam, poor afterfeel |

What is claimed is:

1. An alcohol-free antibacterial wipe comprising:
   a flexible fabric substrate containing a latex binder; and
   an aqueous antibacterial solution, wherein said aqueous antibacterial solution is comprised of an effective amount of a cationic antibacterial agent and a surfactant in an amount sufficient to produce a wet feel to a consumer without further wetting, and said binder is present in at least about 90% of the substrate thickness prior to the addition of the aqueous antibacterial solution to the substrate.

2. The wipe of claim 1 wherein the substrate is further comprised of a front surface and a back surface, and said binder is present on both of the surfaces.

3. The alcohol-free antibacterial wipe of claim 1 wherein said flexible fabric substrate is comprised of rayon,
   said cationic antibacterial agent is benzalkonium chloride, and
   said surfactant is disodium lauroamphodiacetate.

4. The alcohol-free antibacterial wipe of claim 2 wherein the effective amount of benzalkonium chloride is, based upon the total weight of the aqueous antibacterial solution, from about 0.09% to about 0.15%.

5. The wipe of claim 1 wherein the binder is a polymer latex polymerized from at least one acrylic monomer.

6. The wipe of claim 1 wherein the binder is a polymer latex comprised of a mixture of a self-crosslinking acrylic emulsion polymer latex binder and an acrylic emulsion polymer latex binder.

7. A method of preparing an alcohol-free antibacterial wipe which comprises
   (i) preparing a solution of a cationic antibacterial agent, a surfactant, and water; and
   (ii) applying said solution onto a flexible fabric substrate containing a latex binder, wherein said binder is present in at least about 90% of the substrate thickness and wherein said surfactant is used in an amount sufficient to produce a wet feel to a consumer without further wetting.

8. The method of claim 7 which further comprises
   (i) preparing a solution of, based upon the total weight of the solution, from about 0.21% to about 0.22% benzalkonium chloride, about 0.15% to about 0.3% disodium lauroamphodiacetate, and water; and
   (ii) applying said solution onto a substrate comprised of rayon and containing a latex binder, wherein said binder is present in at least about 90% of the substrate thickness.

* * * * *